United States Patent [19]

Romeas et al.

[11] Patent Number: 5,018,176

[45] Date of Patent: May 21, 1991

[54] MAMMOGRAPH EQUIPPED WITH AN INTEGRATED DEVICE FOR TAKING STEREOTAXIC PHOTOGRAPHS AND A METHOD OF UTILIZATION OF SAID MAMMOGRAPH

[75] Inventors: René Romeas, Palaiseau; Didier Rouchy, Les Clayes Sour Bois; Alain Gilleron, Paris, all of France

[73] Assignee: General Electric CGR S.A., Issy les Moulineaux, France

[21] Appl. No.: 497,970

[22] Filed: Mar. 23, 1990

[30] Foreign Application Priority Data

Mar. 29, 1989 [FR] France ................ 89 04086

[51] Int. Cl.$^5$ ............................................. A61B 6/04
[52] U.S. Cl. ........................................ 378/37; 378/196
[58] Field of Search .................................. 378/37, 196

[56] References Cited

U.S. PATENT DOCUMENTS 4,727,565 2/1988 Ericson ................................. 378/37
4,926,453 5/1990 Toniolo ................................. 378/37

FOREIGN PATENT DOCUMENTS 71017 2/1983 European Pat. Off. .
127073 12/1984 European Pat. Off. .
146511 6/1985 European Pat. Off. .
288187 10/1988 European Pat. Off. .
1541671 9/1968 France .

*Primary Examiner*—Craig E. Church
*Attorney, Agent, or Firm*—Oblon, Spivak, McClelland, Maier & Neustadt

[57] ABSTRACT

In order to solve handling problems which arise during use of a mammograph, the x-ray tube of the mammograph is carried by the end of an arm which rotates about an axis at right angles to the arm. The other elements of the mammograph are carried by another arm which is placed in a plane parallel to the plane of rotation of the first arm and rotates about the same axis. It is shown that, by moving the image receiver away from the breast support plate and by utilizing a parallax effect, it is possible to take stereotaxic photographs without entailing any need to displace either the breast support plate or the image receiver or even a radiation-sensitive film placed in a stationary position within the image receiver.

6 Claims, 2 Drawing Sheets

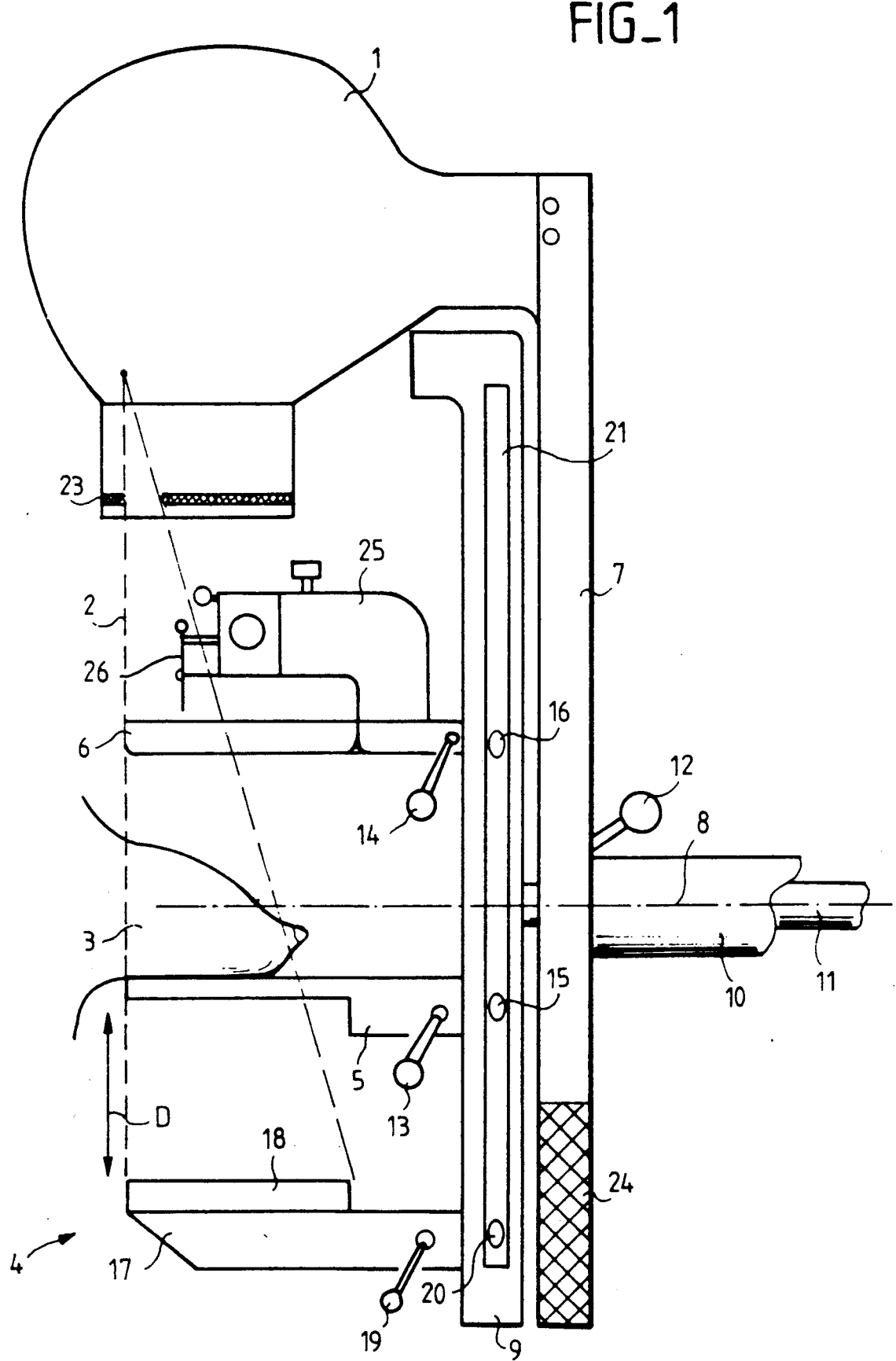
FIG_1

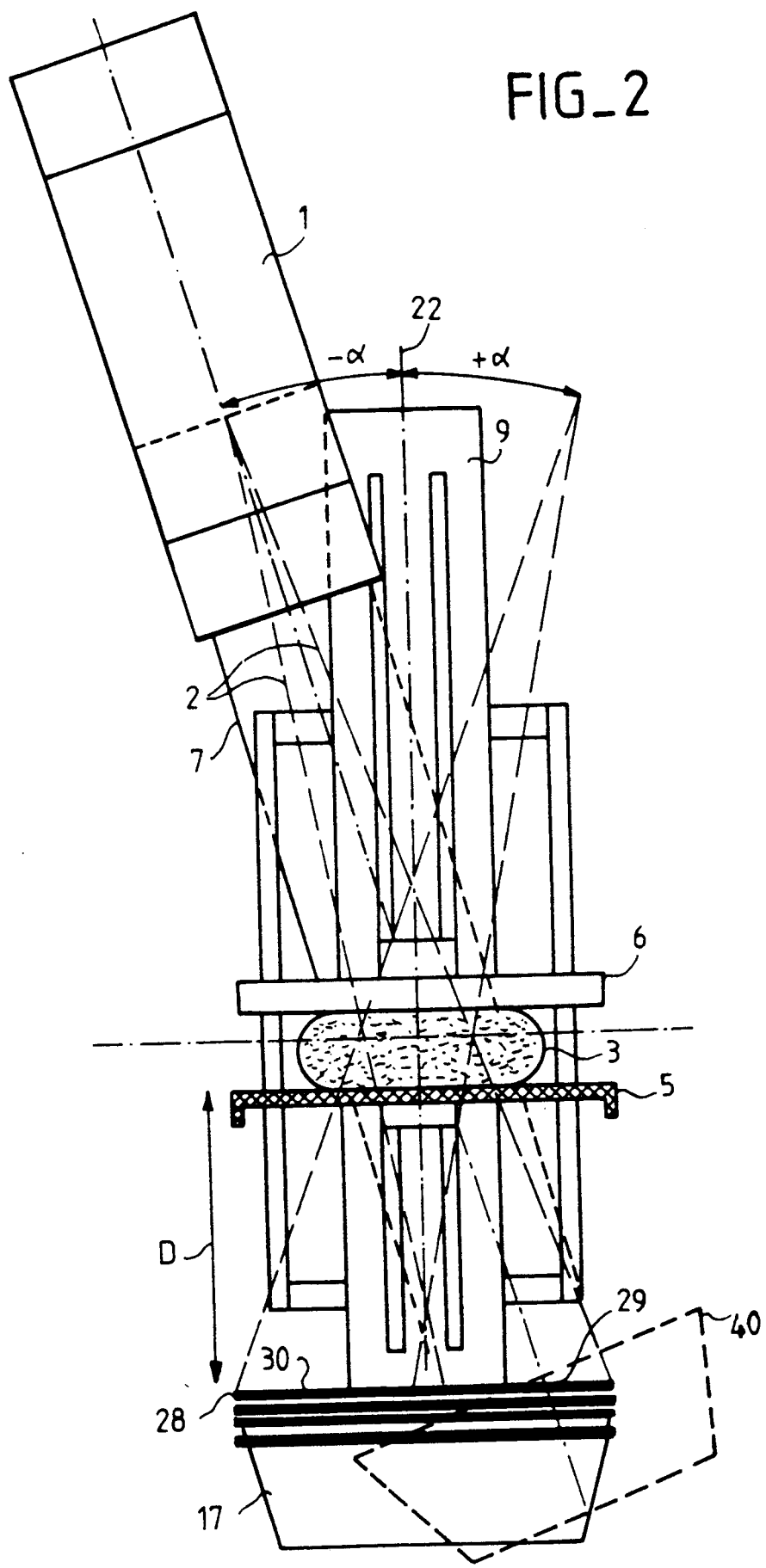
FIG_2

MAMMOGRAPH EQUIPPED WITH AN INTEGRATED DEVICE FOR TAKING STEREOTAXIC PHOTOGRAPHS AND A METHOD OF UTILIZATION OF SAID MAMMOGRAPH

BACKGROUND OF THE INVENTION

1. Field of the Invention

The present invention relates to a mammograph equipped with an integrated device for taking stereotaxic photographs as well as to a method of utilization of said mammograph. The invention is primarily applicable to the medical field in which mammography appears to be the best means of preventive detection or treatment of breast cancer. Stereotaxic photographs are photographs which serve to determine by computation the position of a tumor or of a lesion within a breast under examination.

2. Description of the Prior Art

A mammography apparatus is mainly composed of an arm which is capable of moving about an axis and carries an x-ray generator tube at one end and an image receiver at another end. In the majority of instances, the image receiver comprises a cassette provided with a film and an image intensifier screen. Different devices are interposed on the path of the beam of x-radiation emitted by the tube. Provision is normally made for a beam limiter located upstream in proximity to the x-ray tube. Further downstream and in proximity to a breast support plate, there is provided a breast compression cushion or plate. Said breast support plate and said compression plate are intended to hold the breast in position at the moment of taking of x-ray photographs. They are normally rigidly fixed to the x-ray tube and to the receiver but can be detached therefrom. The fact that the x-ray tube and the image receiver are capable of moving in rotation, if necessary around the breast support plate and compression plate or in fixed relation to these latter makes it possible to take stereotaxic photographs.

In order to produce these stereotaxic photographs, the following procedure is adopted. A second image receiver is employed and fixed near the breast support plate. The x-ray tube which is rigidly fixed to the first image receiver is inclined in a first orientation with respect to the alignment of the breast support plate and the compression plate, a cassette is introduced into the second image receiver and a first photograph is taken. For the first photograph, the cassette is displaced laterally on one side in the second image receiver, with the result that only a first lateral portion of the film contained therein is printed from the first exposure. The cassette is then displaced to the other side within the image receiver, the x-ray tube is inclined in a second orientation and a second photograph is taken. The film corresponding to the two exposures is subsequently developed and, by means of a stereotaxic locating device, the principle of operation of which involves computer processing of the two images obtained, the spatial position of any tumor which may be present is determined, whereupon a biopsy needle is guided with accuracy for therapeutic purposes.

A mammography examination is a relatively unpleasant ordeal for the patient. It is therefore important to take rapid action. On the contrary, the devices in accordance with the present state of the art as described in the foregoing in fact suffer from a disadvantage in that they are slow since it is necessary to displace the cassette between exposures, to develop the film, to compute the position, and to guide the needle, before compression on the breast can be relieved. In the first place, known devices are thus not easy to handle and, in the second place, have a traumatizing effect on patients.

However, these known devices have a wide range of different functions. In particular, they must make it possible to take pictures of the breast at different angles of incidence and especially vertical angles of incidence. It is therefore important to ensure that equipment which is capable of solving the handling problems referred-to above does not do so at the expense of the possibilities of utilization of devices of known type.

When use is made of a larger film cassette which is displaced between the two photographs, the two photographs are not superposed at the two angles of incidence. However, this technique makes it necessary on the one hand to have a zero position reference on each photograph and on the other hand to provide a larger cassette holder in the image receiver. This latter must in fact have a width equal to the length of the cassette plus the length of displacement which is necessary. This may be a cause of difficulty when placing the patient in position, in particular at oblique incidence.

The invention is intended to overcome these disadvantages by proposing two movable elements for supporting the mammograph accessories. These two elements are capable of moving on the one hand with respect to the general support of the mammograph and on the other hand with respect to each other. One of these movable elements carries the x-ray tube whilst the other carries the remainder of the accessories, namely the compression plate, the breast support plate and the single image receiver. The image receiver is thus separated from the x-ray tube. In order to take stereotaxic photographs, the image receiver is also moved aside and this accordingly offers the advantage of a parallax effect which results from relative displacement in projection of the image of a fixed object projected on a fixed image receiver, when the center of projection has moved. The position of the x-ray tube is then simply moved through a predetermined angle which is sufficient to ensure that the two projected images of the breast under radiographic examination are juxtaposed. In order to make this separation of images even more effective, the procedure adopted consists in moving the image receiver away from the breast under radiographic inspection to a distance which is a function of the variation in inclination of the x-ray tube.

SUMMARY OF THE INVENTION

The invention therefore relates to a mammograph comprising means for maintaining opposite to a breast to be radiographically examined on the one hand an x-ray tube and on the other hand a breast support plate and a radiographic image receiver, as distinguished by the fact that the means comprise two arms as follows:
- a first arm which is capable of moving in rotation about a first axis at right angles to said first arm, said first arm being adapted to carry the x-ray tube for orienting the radiation of said tube,
- a second arm which is capable of moving in rotation about a second axis at right angles to said second arm in a plane parallel to the plane of rotation of the first arm, said second arm being adapted to carry the breast support plate and the image receiver, the second arm being provided with means for forming a variable space between the breast support plate and the image receiver so as to ensure that a first image of the breast projected on the image receiver and corresponding to a first orientation of the radiation of the x-ray tube is juxtaposed on said image receiver with a second and different image of the same breast projected under the same conditions but corresponding to a second and different orientation of the radiation of said x-ray tube, these orientations being obtained in respect of different positions of the first arm with respect to the second arm.

The invention is also directed to a method for taking stereotaxic photographs of a breast with a mammograph, in which the following steps are performed:

a breast to be radiographically examined is placed between an x-ray tube and a breast support plate, an image receiver equipped with a radiation-sensitive film is placed downstream of said breast support plate, said image receiver is moved away from said breast support plate and is rigidly fixed to said support plate, the x-ray tube is inclined on one side of the normal to the breast support plate while maintaining said breast support plate and said image receiver in a stationary position, a photograph is taken, the x-ray tube is inclined on another side with respect to said normal without modifying either the position of the radiation-sensitive film or the image receiver, a second photograph is taken, the general image thus obtained is developed, said image being projected in two juxtaposed images on a single radiation-sensitive film introduced in the image receiver.

BRIEF DESCRIPTION OF THE DRAWINGS

FIG. 1 is a schematic sectional presentation of a mammograph in accordance with the invention.

FIG. 2 is a schematic presentation of a front view of the mammograph in accordance with the invention during a stereotaxic picture-taking operation.

DETAILED DESCRIPTION OF THE INVENTION

FIG. 1 shows a mammograph in accordance with the invention. This latter comprises an x-ray generator tube 1 which emits x-radiation 2 in the direction of a breast 3 to be subjected to radiographic examination and in the direction of an image receiver 4. The breast 3 to be examined radiographically is supported by a breast support plate 5 and can be compressed by a compression plate 6. The device in accordance with the invention comprises a first arm 7 which is capable of moving in rotation about a first axis 8 at right angles to said first arm. The axis 8 is substantially horizontal. The x-ray generator 1 is carried by the end of the first arm 7 and fixed thereon by any suitable means. A second arm 9 is also capable of rotating about an axis at right angles to said second arm. Preferably, the axis of rotation of the second arm coincides with the axis 8 of rotation of the first arm 7. A different arrangement could nevertheless be contemplated. In this preferred variant, coincidence of the axes is obtained by constructing a hollow shaft 10 for the rotation of the first arm 7. Within said hollow shaft, an inner shaft 11 is rotatably mounted with precision. The shaft 11 which is secured to the second arm 9 permits rotation of said second arm 9. For certain uses considered hereafter, these two shafts can be coupled together in any position with respect to each other by means of a brake (not shown) actuated by a brake handle 12. Said brake is secured to the shaft 10, for example, and is applied against the shaft 11 when operating the handle 12, thus preventing said shaft from continuing to rotate freely with respect to the shaft 10.

In a known manner, the breast support plate 5 and the compression plate 6 can be adjusted for height on the one hand with respect to each other and on the other hand with respect to the axis 8 of rotation of the first arm 7. A distinctive feature of the invention lies in the fact that handles 13 and 14 for adjusting the heights respectively of the breast support plate 5 and of the compression plate 6 produce action on bolts 15, 16 for locking them respectively in position on the second arm 9. The image receiver 4 comprises a plate 17 which is adapted to receive a cassette 18. Said plate 17 can be adjusted for height by means of a handle 19 which produces action on a latch bolt 20. Said latch bolt 20 maintains the plate 17 with respect to the second arm 9. The latch bolts 15, 16 and 20 can have any shapes. In one example, they can comprise a compressible eccentric which is forcibly engaged within a recess 21 formed in the second arm 9 when the handles 13, 14 and 19 are rotated.

FIG. 2 shows a mode of utilization of the mammograph in accordance with the invention in which stereotaxic photographs of the breast 3 are being taken. The images corresponding to these exposures are transferred in juxtaposition on a film 28 contained in the cassette 18. Possible inclined positions of the x-ray tube 1 carried by the first arm 7 are shown on each side of the axis 22 of the second arm 9 with angles of inclination + or $\beta$. It is observed in the first place that the image receiver 17 is placed at a distance D from the breast support plate 5. The x-radiation can be considered as limited by a limiter 23 (FIG. 1) so that, in a first orientation (inclined to the left), the image of the breast 3 is transferred to the right-hand portion 29 of the film 28. As soon as the photograph has been taken, it is only necessary to tilt the x-ray tube 1 to the other side of the axis 22, preferably through the same angle $\beta$, in order to ensure that the image of the breast 3 is then transferred to the left-hand portion 30 of the film 28. In the meantime, said film has been maintained in its position. It is found that the parallax effect, amplified by the enlargement of images imposed by the spacing D, makes it possible to arrive at the following result: the two images are juxtaposed and no longer coincide.

In consequence, it is possible in a display device or in a processing device to employ the two images thus juxtaposed for exploitation in relief of the breast under study. In practice, an angle $\beta$ of the order of 15° is adopted, thus resulting in a distance D of approximately 25 cm. It is nevertheless possible to choose larger angles $\beta$ and to reduce the spacing D accordingly. In order to permit position-maintenance of the shaft 9 and of all the accessories carried by this latter during this double stereotaxic picture-taking operation, the shaft 11 can be rigidly fixed to a mammograph frame by any suitable means. In the case of stereotaxic photographs, the brake operated by the handle 12 can be released. In this case, the arms are operated from the frame of the mammograph by means of actions applied on the shafts 10 and 11. In a first inclined position of the x-ray tube, the arm 7 is maintained in a predetermined position with respect to the mammograph, preferably by means of stops mounted either on the external frame or on the shaft 8. It is readily apparent that the mammograph frame can have stops corresponding to the other inclination of the x-ray tube on the other side of the axis 22. These stops can be adjustable and can permit explorations (which may or may not be symmetrical) through variable angles (15° to 30°).

However, the mammograph in accordance with the invention can also be employed as a mammograph in accordance with the present state of the technique. To this end, the brake operated by the handle 12 can be applied in such a manner as to ensure that the two arms 7 and 9 are in rigidly fixed relation. When these two arms are locked together while being preferably parallel, the moving arm which they constitute together can be employed for radiographic examinations in the same manner as an ordinary arm. FIG. 2 shows in dashed outline, in the case of a locking operation of this type, the corresponding position 40 of the image receiver in the case of a conventional photograph taken at an oblique angle of incidence $-\beta$. At this oblique angle of incidence $-\oplus$, the representation of the breast support plate and of the compression plate is not shown but should be inclined with respect to the arrangements shown.

It is possible that the limiter 23 may not prove sufficient to prevent fogging of that portion (30) of the film which corresponds to another photograph at the moment of taking of a first photograph (29). With this objective, a mask for protecting that part of the film 28 which is not to be exposed can be displaced by hand or preferably associated in common movement with the arm 7. For example, two elbowed rods can be placed in proximity to the counterweight 24 of the x-ray tube 1 on the arm 7. The ends of said rods are intended to transmit motion to the edges of a flat mask which has an open central portion so as to allow radiation to pass and which is placed above the image receiver 4. The position of the opening of the mask therefore follows substantially the useful trace of the x-radiation. If necessary, provision can be made for a motor drive and for electrical control of the position of the mask.

In comparison with the displacement of cassettes of the prior art, the displacement of a mask in this case has an advantage in that the film remains in place and its position is therefore automatically adjusted in the cassette. The result thereby achieved is that the calculations which could be made with the same film but doubly exposed in accordance with the invention will contain a smaller number of errors than those calculations which could be made by comparing two photographs taken by displacing the cassette within its housing. With the invention, there is in fact no need to be concerned with position setting of one photograph with respect to the other. Irrespective of the positioning of the cassette 18 on the cassette-holder 17, the two images are located in coherent positions with respect to each other. This results in a more accurate interpretation of the stereotaxic views. In consequence, a biopsy needle holder device 25 fitted with a needle 26 and fixed on the compression plate 6 can be moved with very high precision towards a part of the breast 3 in which it is desired to take a sample. A position reference of said needle-holder can be very easily obtained by replacing the needle by a small metal ball (or a cross) judiciously placed at a known location on the needle-holder. The trace of said ball is visible on each photograph and provides a reference in regard to the position of the needle-holder with respect to the breast under radiographic examination.

Owing to the ease with which it can be handled, the mammograph in accordance with the invention makes it possible to dispense with the greater part of the additional devices of the prior art. These devices were necessary for stereotaxic photography. In practice, the weight of the additional device constituted by the second arm 9 is of the order of three or four kilograms whereas the weight of the additional devices was approximately fifteen kilograms in the prior art. It was in fact also necessary to use other compression plates 6, other breast support plates 5 and other cassette-holder plates 17, and other compression devices.

The invention is also distinguished by the ingenious mode of utilization of a mammograph. In this mode of utilization, the image receiver is moved to a distance D from the breast support plate and the x-ray tube alone is displaced on each side of the normal while maintaining the image receiver in position for each photograph. In consequence, the photographs obtained benefit by enhanced accuracy of the locating device.

What is claimed is:

1. A mammograph comprising means for maintaining opposite to a breast to be radiographically examined on the one hand an x-ray tube and on the other hand a breast support plate and a radiographic image receiver, wherein said maintaining means comprise two arms as follows:
    a first arm which is capable of moving in rotation about a first axis at right angles to said first arm, said first arm supporting the x-ray tube, for orienting the radiation of said tube,
    a second arm which is capable of moving in rotation about a second axis at right angles to said second arm and in a plane parallel to the plane of rotation of the first arm, said second arm being adapted to carry the support plate and the image receiver,
    the second arm being provided with means for forming a variable space between the breast support plate and the image receiver so as to ensure that a first image of the breast projected on the image receiver and corresponding to a first orientation of the radiation of the x-ray tube is juxtaposed on said image receiver with a second image of the same breast projected under the same conditions but corresponding to a second orientation of the radiation of said x-ray tube, these different orientations being obtained in respect of different positions of the first arm with respect to the second arm.

2. A mammograph according to claim 1, wherein the two axes of rotation of the two arms are collinear and substantially horizontal.

3. A mammograph according to claim 1, wherein said mammograph comprises means for locking the relative movements of rotation of one arm with respect to the other in any position.

4. A mammograph according to claim 1, wherein the second arm carries in addition a breast compression plate which is in turn fitted with a biopsy needle holder.

5. A mammograph according to claim 1, wherein the breast support plate and the radiographic image receiver are attached to the second arm by means for displacing these two elements in sliding motion along said arm.

6. A method for taking stereotaxic photographs of a breast with a mammograph, wherein said method involves the following steps:
- a breast to be radiographically examined is placed between an x-ray tube and a breast support plate,
- an image receiver equipped with a radiation-sensitive film is placed downstream of said breast support plate,
- said image receiver is moved away from said breast support plate and is subsequently fixed to said support plate,
- the x-ray tube is inclined on one side of the normal to the breast support plate while maintaining said support plate and said image receiver in a stationary position,
- a photograph is taken,
- the x-ray tube is inclined on another side with respect to said normal without modifying either the position of the radiation-sensitive film or the image receiver,
- and a second photograph is taken,
- the general image thus obtained is developed, said image being projected in two juxtaposed images on a single radiation-sensitive film introduced in the image receiver.

* * * * *